United States Patent [19]

Gardy

[11] Patent Number: 4,676,240
[45] Date of Patent: Jun. 30, 1987

[54] TONGUE LOCKING DEVICE TO MINIMIZE EFFECTS OF SLEEP APNEA AND TO REDUCE SNORING

[76] Inventor: Victor R. Gardy, 32 Richmond Dr., Shelburne, Vt. 05482

[21] Appl. No.: 773,991

[22] Filed: Sep. 9, 1985

[51] Int. Cl.[4] .......................................... A61M 15/00
[52] U.S. Cl. ................................ 128/207.14; 128/136
[58] Field of Search .......... 128/DIG. 12, 136, 204.13, 128/200.24

[56]  References Cited

U.S. PATENT DOCUMENTS

| 2,589,504 | 3/1952 | Miller | 128/136 |
| 3,211,143 | 10/1965 | Grossberg | 128/136 |
| 3,448,738 | 6/1969 | Berghash | 128/136 |
| 3,692,205 | 9/1972 | Greenberg | 128/136 |
| 3,864,832 | 2/1975 | Carlson | 128/136 |
| 4,169,473 | 10/1979 | Samelson | 128/136 |
| 4,170,230 | 10/1979 | Nelson | 128/136 |
| 4,196,724 | 4/1980 | Wirt et al. | 128/136 |
| 4,262,666 | 4/1981 | Nelson | 128/204.13 |
| 4,304,227 | 12/1981 | Samelson | 128/136 |
| 4,593,686 | 6/1986 | Lloyd | 128/136 |

FOREIGN PATENT DOCUMENTS 65194 11/1892 Fed. Rep. of Germany .
2704709 8/1977 Fed. Rep. of Germany .

OTHER PUBLICATIONS

Silastic Artificial Eustachian Tube by James W. Donaldson, the Bulletin of the Dow Corning Center for Aid to Medical Research, vol. 7, No. 1.

Primary Examiner—Carlton R. Croyle
Assistant Examiner—Jane E. Obee

[57] ABSTRACT

A device is provided for positioning within the mouth of a user to hold the tip of the tongue forward of the teeth so as to increase pharyngeal airflow passageway and provide oral airflow passageway and thus mimimize sleep apnea effects and signifcantly reduce snoring. The device is an integrally molded body of pliable elastomeric material universally fitted to most tongue sizes when the tongue is inserted into a rearwardly-opening central vacuum chamber, it displaces the air in the chamber. Then, when the tongue relaxes in the deep stages of sleep it is held forward in the vacuum chamber by the vacuum it automatically creates as it attempts to retract since it is sealed by means of internal ridges around all sides of the tongue and located closer to the rear of the vacuum chamber. The tongue retractive force is reacted through the device by teeth engaging portions of the device. When the tongue is thus held forward of its usual restive postion behind the dental arches, the dimension of air passage around the soft palate, the uvula, and the posterior pharyngeal wall is increased and breathing is facilitated through the nasopharynx, and also, through the oro-pharynx by means of perforations provided alongside the vacuum chamber to provide communication between the mouth cavity and the external environment to allow oral breathing and lower breathing pressure. The device substantially improves breathing through both the nose and mouth, automatically during sleep thus minimizing the effects of sleep apnea and reducing snoring.

2 Claims, 2 Drawing Figures

TONGUE LOCKING DEVICE TO MINIMIZE EFFECTS OF SLEEP APNEA AND TO REDUCE SNORING

This invention relates to increasing the size of the air passageway through the oro- and naso-pharynx during sleep by means of holding the tip of the tongue forward of the dental arches along with providing for oral air passages, and thus, to significantly reducing the harmful effects of obstructive sleep apnea and disruptive snoring.

BACKGROUND OF THE INVENTION

Sleep apnea gives rise to the condition where the tongue relaxes and contributes to blocking of the air passageway in the pharynx for breathing from the nasal and oro openings. Further, loose tissue, including the tongue, the pharyngeal folds, the soft palate, the muscular uvulae and the palate-pharyngeal arch, tend to vibrate as air flows past, especially in a high pressure forced condition causing vibration observed as snoring. In prior patents reviewed, various contradictions were evident as to the method of preventing snoring. U.S. Pat. Nos. 1,774,446 and 3,434,470, and British Pat. No. 1,248,474, propose to insure that oral breathing occurred. Whereas, U.S. Pat. Nos. 4,169,473 and 4,304,227, propose to completely block oral breathing to prevent snoring.

In addition, those and others, in particular, U.S. Pat. Nos. 4,169,473 and 4,304,227, propose holding both dental arches in a locked position which can be detrimental to the normal bite relationship of the dental arches. Such condition causes jaw arches and distorts the normal biting relationship of the upper and lower jaws. This device allows freedom of that relationship by anchoring only to one dental arch and allows the other jaw to float to any relaxed position. Other patents reviewed in this related field were U.S. Pat. No. 3,211,143, and 3,448,738, and 3,692,205, and 4,196,724, and Fed. Rep. of Germany Nos. 65194, and 2704709. Wirt, U.S. Pat. No. 4,196,724, defines a means for sucking out air to create a vacuum, whereas this application defines an automatically created vacuum when the tongue tries to withdraw from the sealed chamber, and Samelson, U.S. Pat. Nos. 4,169,473, and 4,304,227, defines "sucking" out of air and imperforate structure to prevent oral breathing as opposed to this application which provides oral breathing holes to aid in lowering breathing pressure. It was sincerely believed that none of them operated in this manner nor have achieved what this tested and proven device has in regard to relieving effects of sleep apnea and reducing snoring.

It is the object of this invention to help keep open the air passageway in the pharyngeal area as much as possible during sleep by automatically holding the tip of the tongue forward of the dental arches and to provide oral breathing passageways, which action, in combination, significantly reduces the harmful effects of obstructive sleep apnea and disruptive snoring by allowing relaxed low pressure breathing rather than forced high pressure breathing.

BRIEF SUMMARY OF THE INVENTION

This invention is adapted for insertion into the mouth of the user for holding the tongue forwardly, and enlarging the internal naso- and oro-pharynx air passageways to enhance relaxed breathing. The device includes a molded body for entry into the mouth to engage either one of the user's teeth or gum arches to anchor the device in position and react the tongue pulling force. The vacuum chamber with a closed forward end extends rearwardly, with the rear end of the chamber being open. It is shaped open to receive a part of the forward end of the user's tongue. When operatively positioned within the mouth, the user's tongue forms itself to and fills the chamber opening and displaces the air in the chamber upon entry and is sealed by the internal sealing ridges located on the inside of the vacuum chamber near the rear end with the aid of the specific material properties and structural sizing flexibility. As the relaxing tongue tends to pull rearward it automatically creates a negative pressure within the vacuum chamber by means of the sealing ridges surrounding the tongue in the vacuum chamber near the rearward end and by the force of the relaxing tongue whose pulling force is resisted through the device structure by the outer ridges that engage either of the dental arches. The other unengaged dental arch is allowed to float, thus preventing any disturbance to the normal biting position. The position of the tongue, when so secured, is thus held forward of its normal resting position behind the dental arches. Since the body of the tongue is held forwardly of its normal proximity to the soft palate, the uvula and the posterior pharyngeal wall, an increase in the size of the air passage way is provided while additional oral air passageway is provided in the structure, thus in combination allowing relaxed breathing and minimizing the effects of sleep apnea and reducing snoring. Some structural flexing also helps maintain the seal around the rear internal sealing ridges of the vacuum chamber. Any slight biting pressure also helps maintain the seal. Further, since the device thickness prevents the jaws from fully closing, the air passageway is thus additionally increased by the partial opening of the jaws which positions even further forward the anchoring bone on the lower jaw structure to which the tongue is attached thus placing the tongue even further forward with it. Additionaly in combination with the above, holes are molded into the structure to allow passage of air through the oro opening, thus allowing airflow at lower pressure and minimizing vibration of the aforementioned pharyngeal breathing area.

DETAILED DESCRIPTION OF THE INVENTION

Figure 1:
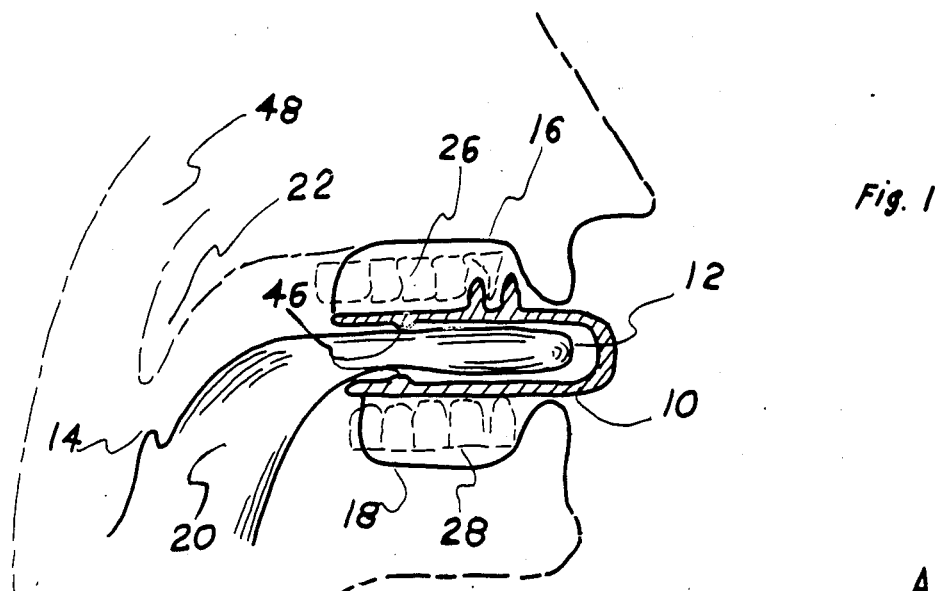
FIG. 1 is a vertical cross-sectional view along the longitudinal axis of line A—A of FIG. 2 illustrating the device operatively positioned in the mouth of the user showing the positin of the tongue, jaws and air passageway.
Figure 2:
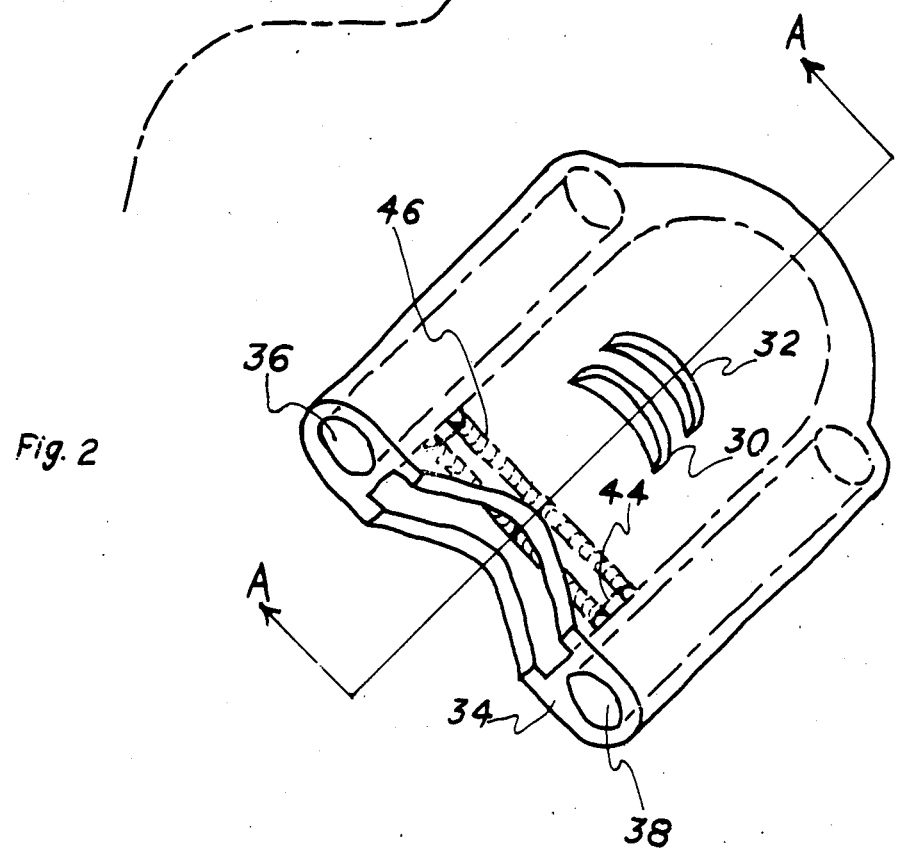
FIG. 2 is a perspective view of the embodiment of the invention showing the dental restraining ridges, the oral passage openings, and the internal vacuum chamber with internal sealing.

Referring to the drawings, the tongue holding device of this invention is shown generally as 10 in FIGS. 1 and 2. The specific device comprises a tongue receiving vacuum chamber 12 for holding the tongue forward and increasing the breathing passage 14. It is sized to be universally adaptable to most tongue sizes by means of the flexibility of the elastomer material which is sufficient to maintain the vacuum seal with the aid of internal sealing ridges, thus avoiding the need for special fitting by a dentist. It protrudes forward of the lips outside of the mouth and extends rearwardly to near the rear of the dental arches. FIG. 1 depicts the usual anatomical structure of the mouth of a user of the invention. The mouth includes the upper jaw 16, the lower jaw 18, the tongue 20, and the soft palate or musculus uvulae 22 hanging downwardly approximate the base of the tongue, the posterior pharyngeal wall 24, and the upper and lower dental arches comprising upper and lower teeth 26 and 28. The protruding ridges 30 and 32 comprise the restraining device for the tongue pulling force, reacting against either of the dental arches. They are placed only on one side so as to allow free movement of the other jaw or dental arch, thus not interfering with the natural bite position. As the tongue tends to fall rearward during sleep, a vacuum is created in the vacuum chamber, being sealed, thus maintaining the relative position of the body of the device to the tongue. This tendency is resisted by the dental arch engaged in the outer restraining ridges. The device thickness 34 provides the resistance to full jaw closure. The two through holes 36 and 38 allow airflow through the mouth during normal use and especially when the nasal passage is clogged with mucus in times of a cold or flu or swelled by allergy reactions.

FIG. 2 shows more defined views of the tongue pulling force restraining ridges 30 and 32, and of the internal sealing ridges 44 and 46 of the tongue holding vacuum chamber. In addition to the elastomer material flexibility helping provide the seal around the tongue, any slight biting pressure from the dental arches also aids in maintaining the vacuum seal, utilizing the pliability of the tongue.

The device, successfully tested by me, is specifically molded from elastomer materials that are medically approved.

OPERATION

The device 10 is positioned in the mouth of the user such that the outer ridges 30 and 32 engage either of the dental arches. The user then extends his tongue into the vacuum chamber 12 displacing the air within. A seal is thus formed around the tongue 20 and the internal vacuum chamber sealing edges 44 and 46. Later, as the user falls asleep the tongue relaxes and tries to withdraw from the vacuum chamber. As it does so it creates a vacuum sufficient to resist the rearward pull of the tongue, thus holding the tongue forward and allowing a significantly increased air passage through the pharyngeal area, whether incoming from the nasal passage 48 or the oral passage through the openings 36 and 38. The pull of the tongue is resisted by the vacuum, sealed by the inner ridges to the body, and thence by the outer ridges 30 and 32 reacting against the dental arch engaged. By maintaining the tongue in the forward position, and providing air passageway through the mouth, the air passageway openings are increased thus allowing freeflow and low air pressure breathing. Consequently the effects of sleep apnea are minimized and snoring is also reduced.

While a particular form of my invention has been disclosed and described, it will be understood that the invention may be utilized in other forms and for other purposes, so that the purpose of the appended claims is to cover all such forms of devices not disclosed but which embody the invention disclosed herein.

What is claimed and desired to be secured by Letters Patent of the United States is:

1. A device to minimize the effects of sleep apena and significantly reduce snoring, by holding the tongue forward of its usual resting position with a vacuum holding force and resisting the tongue's tendency to fall back during sleep by means of a universally adaptable tongue sized vacuum chamber, internal sealing ridges, structural flexibility, and reactive force connection to the dental arches, comprising, in combination:

an elastomeric material structure of size and shape to be removably positioned in the user's mouth, to be held therein by one of the user's dental arches, being shaped to provide ridges on each side of either the user's upper or lower dental arch, and a vacuum chamber of engageable means that is shaped to define a rearwardly opening vacuum chamber for receiving the tongue with oral airflow passages in parallel along both sides of the vacuum chamber to provide communication between the mouth cavity and the external environment to allow oral breathing, the vacuum chamber having a forward closed end and a rearward open end, shaped to universally fit over most tongues, therein to effect an airtight seal therewith when, upon insertion of the tongue into the vacuum chamber, air is thus displaced from the forward portion of the vacuum chamber past the tongue, such that negative pressure, created automatically, and only, when the tongue tends to withdraw during sleep relaxation, causing a vacuum, which is sealed on all sides by the internal sealing ridges near the rear end of the vacuum chamber and maintained by the flexibility of the elasotmeric material structure, which adapts to most size tongues while maintaining sufficient pressure to create a seal, aided by any slight biting pressure of the jaws that provides sealing reinforcement, whereby the tongue is then held forwardly of its usual resting position behind the teeth, thereby holding the remainder of the body of the tongue forward from its normal proximity to the soft palate, the uvula and the posterior pharyngeal wall, to form and maintain an airway of increased size through the naso- and oro-pharynx, in combination with the oral airflow passage in the body of the device, which allow passage of air through the mouth also thus lowering breathing pressure and minimizing the effects of sleep apnea and reducing snoring.

2. A device as in claim 1 wherein the vacuum chamber includes internal sealing ridges on all internal sides, such that the inserted tongue is surrounded on all sides by the sealing ridges, for the purpose of sealing the vacuum between the vacuum chamber and the tongue, located between the front and rear ends of the vacuum chamber and closer to the rear open end of the vacuum chamber.

* * * * *